United States Patent [19]
Holtsch

[11] Patent Number: 5,314,437
[45] Date of Patent: May 24, 1994

[54] CONSTRICTING DEVICE FOR BODY PARTS

[75] Inventor: Peter Holtsch, Taunusstein, Fed. Rep. of Germany

[73] Assignee: Holtsch Metallwarenherstellung Inh. Maria Holtsch, Taunusstein, Fed. Rep. of Germany

[21] Appl. No.: 45,616

[22] Filed: Apr. 9, 1993

[51] Int. Cl.⁵ ..................... A44B 11/06; A61B 17/12
[52] U.S. Cl. .................... 606/157; 606/151; 606/203
[58] Field of Search ............... 606/1, 138, 141, 144, 606/145, 148, 149, 150, 151, 157, 158, 213, 203; 600/36, 37

[56] References Cited

U.S. PATENT DOCUMENTS

| | | | |
|---|---|---|---|
| 3,667,471 | 6/1972 | Doty et al. | 606/158 |
| 4,800,879 | 1/1989 | Golyakhovsky et al. | 606/158 |
| 5,203,786 | 4/1993 | Vernick | 606/151 |
| 5,226,429 | 7/1993 | Kuzmak | 606/157 |

FOREIGN PATENT DOCUMENTS 0804636 10/1936 France .................. 606/139

*Primary Examiner*—Stephen C. Pellegrino
*Assistant Examiner*—Glenn Dawson
*Attorney, Agent, or Firm*—Michael J. Striker

[57] ABSTRACT

A constricting device for body parts, has a housing, a clamping rocker supported in the housing rotatable between a clamping position in which one end of the clamping rocker clamps a band extending through the housing against a housing wall and an opposite releasing position in which it releases the band, so that the clamping rocker in a constriccting position of the band which is under tension is turned to the clamping position while a manual pressure applied to the clamping rocker turns the latter to the releasing position. A releasable arresting closure is provided between another end of the clamping rocker and an end of the band at the side of the housing, and a mechanical transmission member which during application of an actuating pressure to the clamping rocker first turns the clamping rocker to the releasing position and then after a release of the band opens the arresting closure.

8 Claims, 9 Drawing Sheets

CONSTRICTING DEVICE FOR BODY PARTS

BACKGROUND OF THE INVENTION

The present invention relates to a constricting device for body parts, in particular to a vein constrictor.

More particularly, it relates to a constricting device for body parts which has a housing, a clamping rocker turnably supported in the housing and having one end for clampingly pressing a band extending through the housing against a housing wall in a clamping position and for releasing the band in an opposite releasing position, and a releasable arresting closure between another end of the clamping rocker and a cap for fixing an end of the band to the housing.

The band which is usually elastic forms a loop around the body part to be constricted. When the band is tightened by pulling of its free end, the force which occurs at the end connected to the housing, turns the clamping rocker to its clamping position in which it arrests the band in its constricting condition. When the constriction must be ended without removing the loop from the body part, since shortly after this a new constriction can be needed, it is sufficient to apply a finger pressure on the clamping rocker, directly or by means of an intermediate member, to turn the same to its releasing position in which the band can be moved back through the housing and the restricting tension can be removed. When the work with the restricting device is completely finished, the arresting closure is released and the loop around the body part can be removed without pulling the band with its free end through the closure housing.

Such a vein constrictor is disclosed, for example in the German document DE-U-92 00 574.8 and has been recommended in practice. The both functions of the band tensioning or releasing on the one hand and the band opening on the other hand provide for a good adaptation of the device to different applications with fast handling of the restricting device. On the other hand, the separation of both functions requires separate hand gripping for the actuation of the device.

SUMMARY OF THE INVENTION

Accordingly, it is an object of the present invention to provide a constricting device for body parts, which avoids the disadvantages of the prior art.

In keeping with these objects and with others which will become apparent hereinafter, one feature of the present invention resides, briefly stated, in a constricting device provided with a mechanical transmission member which, during application of an actuating pressure, first turns the clamping rocker to its releasing position and then after the release of the band opens the arresting closure. In this manner, a "single organ actuation" of the constricting device is provided. It is no longer necessary to perform different operations for obtaining the above mentioned both functions of the device.

Moreover, the device designed in accordance with the present invention eliminates the danger that an opening of the band loop on the arresting closure from the constricting position of the band (under tensioning of the band) can scare the patients who use the constricting device or injure them and can lead, for example during the blood taking, to a spontaneous change in the blood pressure. Moreover, it is guaranteed that the band loop can be open only when an available restricting tension in the band is removed.

The device in accordance with the present invention can be made in different structural ways. In accordance with a first alternative, during turning of the clamping rocker from its clamping position, the transmission member provides in the releasing position of the clamping rocker the operative connection with the arresting closure and opens the same during further turning of the clamping rocker to an opening position. The transmission member (or several transmission members) can be arranged between the clamping rocker and the arresting closure. It can be also formed as an additional actuating element which over its initial actuating path first turns the clamping rocker to its releasing position and during the subsequent actuating path opens the arresting connection.

In such a construction a "pressure point" of the transition from the clamping rocker actuation to the arresting closure actuation can be identified in that, for example the transmission member must overcome, during the applying actuation pressure to the clamping rocker for opening the arresting closure, a greater resistance than during the release of the band. This is performed in particular in that the closing force of at least one spring which presses the arresting closure to its closing position counteracts the opening actuation with a greater force component than the band in its constricting position applies to the clamping rocker in the clamping direction.

A reliable time separation of the arresting closure opening from the preceding releasing of the band tension can be obtained when a catch blocks the efficiency of the transmission member until an interruption of the actuating pressure after the release of the band. In order to perform the second stage of the actuation and in particular the opening of the arresting closure, the operator must unload the corresponding actuating element shortly before the actuating pressure. When the actuating pressure is again applied, the opening of the band loop is performed. In the intermediate time the constricting tension can reliably build up in the band.

In all above mentioned cases the actuating pressure is applied directly to the clamping rocker which is arranged in engagement or can come to engagement with the transmission member (or the transmission members). However, also intermediate members for the actuation of the clamping rocker on the one hand and the arresting closure on the other hand can be provided. For example a push button or a sliding button can be arranged in articulated operating connection with the clamping rocker, so that during the operation the buttons can engage first with the clamping rocker and then with the components of the arresting connection.

In accordance with an especially advantageous embodiment of the catch which interrupts the actuating sequence, a swinging bearing of the clamping rocker can be longitudinally displaceable in the housing and the band in its constricting position can pull the clamping rocker against the force of a spring to a first end position. In this position during pressure actuation of the clamping rocker, a stop limits its turning movement to reaching the releasing position until after release (and pull unloading) of the band the spring moves the clamping rocker to its second end position in which it can be turned to its opening position and therefore open the arresting closure. Advantageously the stop has a substantially rectangularly extending portion which prevents the longitudinal movement of the clamping rocker under the spring force ("catch nest"), until the clamping rocker is turned back to its releasing position.

The novel features which are considered as characteristic for the invention are set forth in particular in the appended claims. The invention itself, however, both as to its construction and its method of operation, together with additional objects and advantages thereof, will be best understood from the following description of specific embodiments when read in connection with the accompanying drawings.

DESCRIPTION OF THE PREFERRED EMBODIMENTS

Figure 1:
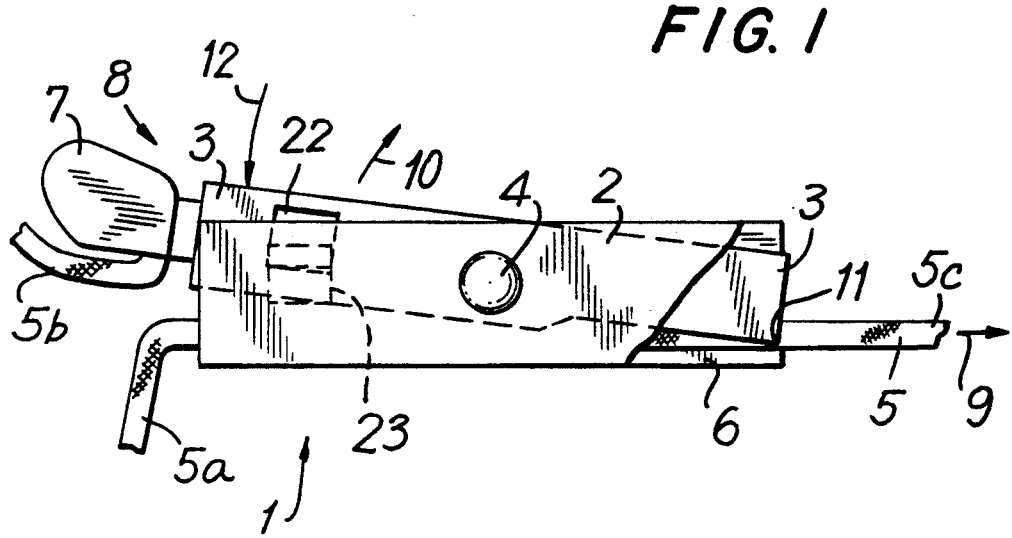
FIG. 1 is a side view of a constricting device in a constricting position of the housing.
Figure 2:
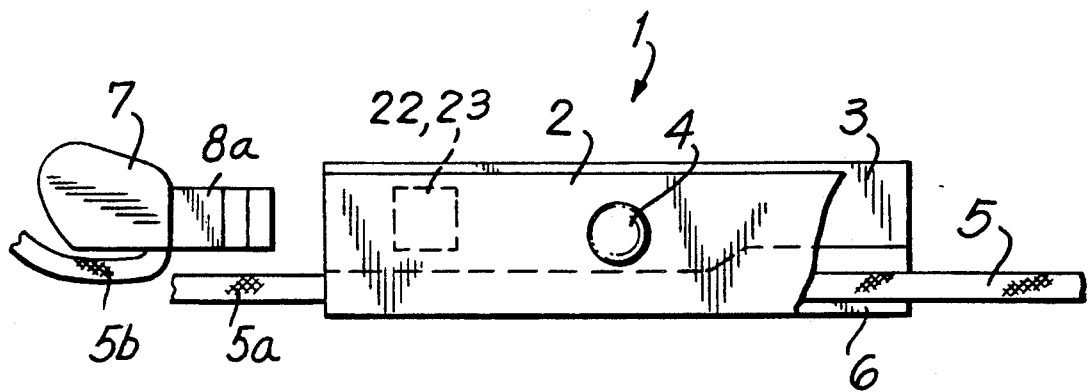
FIG. 2 is a side view substantially corresponding to the view of FIG. 1 in an opening position.
Figure 3:
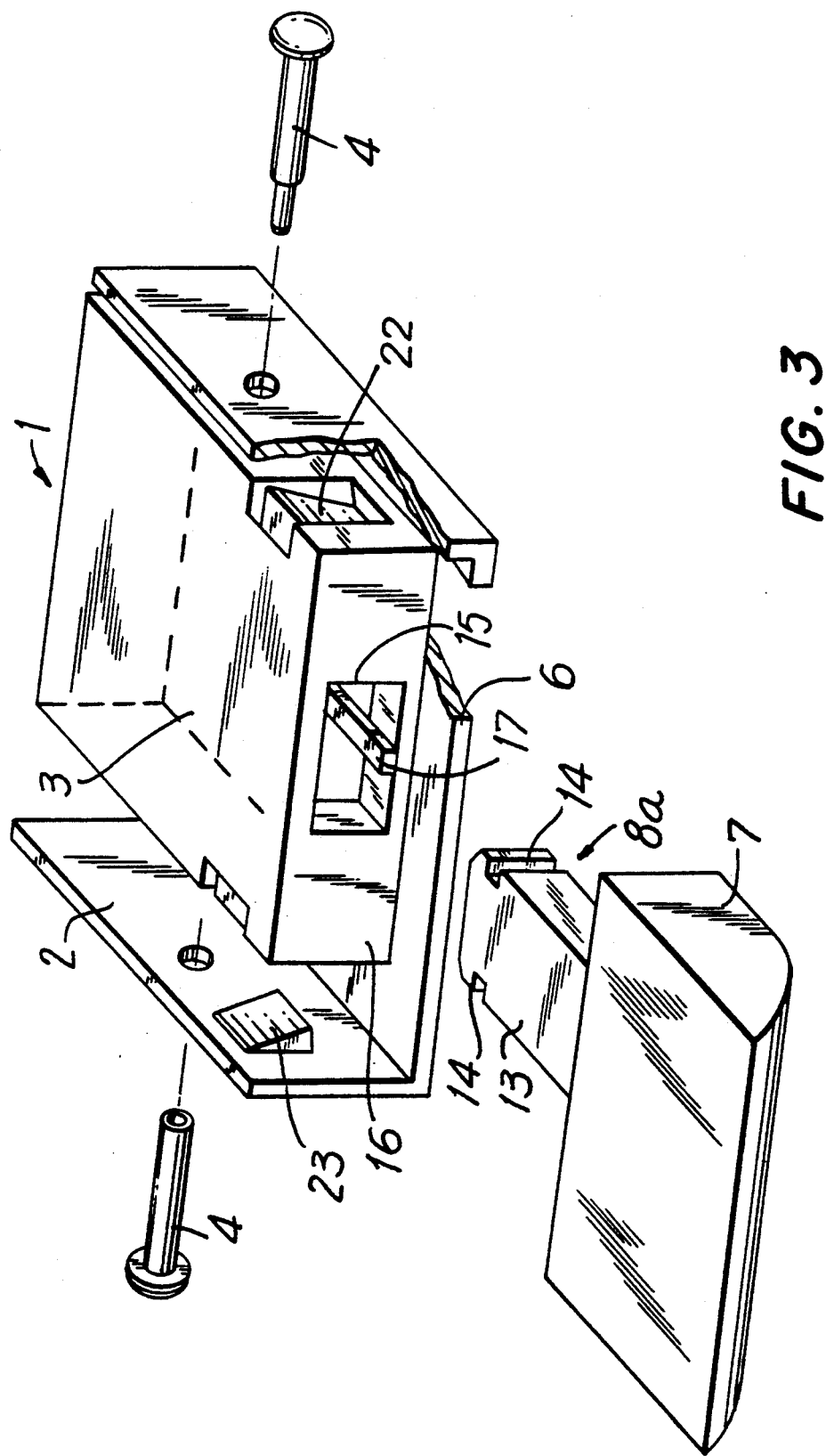
FIG. 3 is a perspective explosion view of substantial parts of the closure housing and an arresting closure.

A constriction device in accordance with the present invention has a closure 1 with a closure housing 2. The closure housing 2 has a cross-section in form of a wide U as shown in FIG. 3 but can be also at least partially closed above as shown for example in FIGS. 7-10 and 13-17. A clamping rocker 3 is turnably supported in the housing substantially centrally by means of a pin 4 composed of two parts as shown in FIG. 3. A constricting band 5 runs between a bottom portion 6 of the housing 2 and the clamping rocker 4. It forms a bent loop which is shown at the left side of FIG. 1 with its bent portions 5a and 5b. The band end at the side of the housing is mounted with the portion 5b in a cap 7. The cap 7 carries a component 8a of an arresting closure which is identified as a whole with reference numeral 8. Another component of the arresting closure which is not shown in FIGS. 1 and 2 is located in the clamping rocker 3. The arresting closure 8 in FIG. 1 is closed, or in other words is fixed in the clamping rocker 3. The band 5 is pulled at its free end 5c in the direction of the arrow 9 through the closure housing 2. Due to the constricting pulling force which is oriented inclinedly outwardly in the portion 5b of the band 5, the clamping rocker 3 is turned upwardly in direction of the arrow 10. Thereby its clamping edge 11 engages in the band 5 and arrests it against a return sliding opposite to the arrow direction 9.

When a pressure is applied in the region and in direction of the arrow 12 to the clamping rocker 3, the clamping rocker turns against the arrow 10 around its axle 4. The clamping edge 11 releases the band 5, and the band 5 due to the restoring force in the band can slide automatically and in the constricted body part against the arrow 9 through the closure housing 2. The releasing position is obtained thereby.

A further turning movement of the clamping rocker 3 under the action of the pressure applied in direction of the arrow 12 leads to opening of the arresting closure 8. The cap 7 with the arresting component 8a on the band portion 5b and therefore at the housing end of the band 5 is released from the clamping rocker 3. Thereby the opening position shown in FIG. 2 is obtained.

FIGS. 3-6 show the construction for obtaining the releasing and opening sequence of the closure 1 (with the arresting closure 8). The arresting component 8a on the cap 7 has a tongue 13 which in the region of its free end forms two laterally extending hooks 14 arranged mirror-symmetrical to a longitudinal axis 19. The tongue 13 can be inserted in an opening 15 in an associated end side 16 of the clamping rocker 3. A central guide 17 in the clamping rocker engages in a not shown groove in the lower side of the tongue 13.

In the arrested condition which is not shown in the drawings the hooks 14 of the tongue 13 of the arresting component 8a engage behind arresting cams 18 of two sliders 20. The sliders 20 are mirror-symmetrical relative to the longitudinal axis 19 and are transversely displaceable in the clamping rocker 3. Spring tongues 21 which ar located opposite to the arresting cams 18 abut on the corresponding other hooks 14 and their spring force produced in the arresting condition by the elastic deflection guarantees that the sliders 20 cannot perform undesired transverse movement and therefore release the arresting connection between the arresting cams 18 and the hooks 14. Such an arresting closure is known for example from the German document DE-U-92 00 574.8.

In contrast to the known arresting closure the sliders 20 do not run however in lateral and outwardly accessible push buttons which serve for opening the arresting closure, namely for moving the arresting cams 18 in opposite directions against the force of the spring tongues 21. Moreover, as can be seen from FIGS. 3 and 5, they are laterally provided with wedge surfaces 22 which abut against corresponding oppositely inclined wedge surfaces 23 on the side walls of the closure housing 2 and engage with them. As can be seen from FIG. 5, by applying a pressure to the clamping rocker in direction of the arrow 12 in FIG. 1, first the releasing position and thereby the release of the band 5 by the clamping edge 11 of the clamping rocker 3 is obtained. Immediately after this, during further pressing in direction of the arrow 12 and therefore further turning of the clamping rocker against the arrow 10, the wedge surfaces 23 of the closure housing 2 in cooperation with the wedge surfaces 22 of the sliders 22 are displaced relative to one another so far that they move from the arresting position shown in FIG. 5a to the opening position of the arresting closure 8 shown in FIG. 5b, and the cap 7 with the component 8a is ejected from the opening 15 of the clamping rocker 3.

Figure 4:
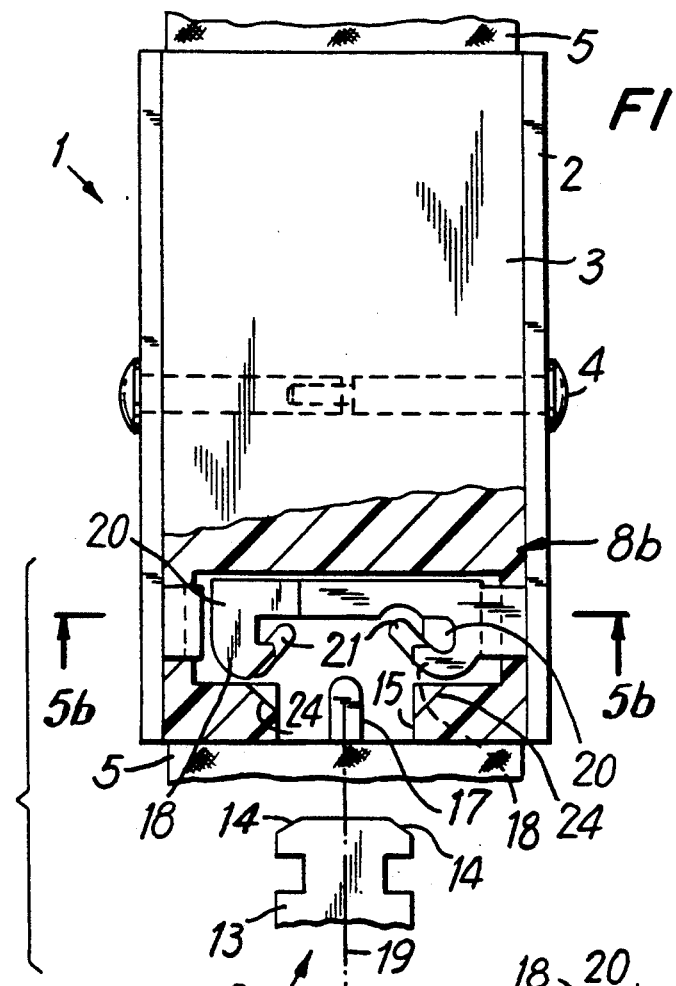
FIG. 4 is a partially sectioned plan view of the arrangement shown in FIG. 2.
Figure 5A:
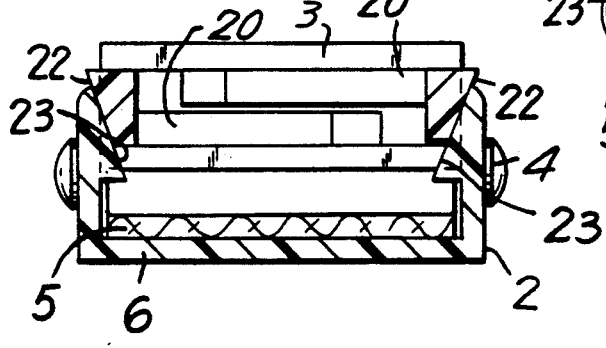
FIGS. 5a and 5b are views showing two cross-sections taken along the line V—V in FIG. 4 in a constricting position and in an opening position correspondingly.
Figure 5B:
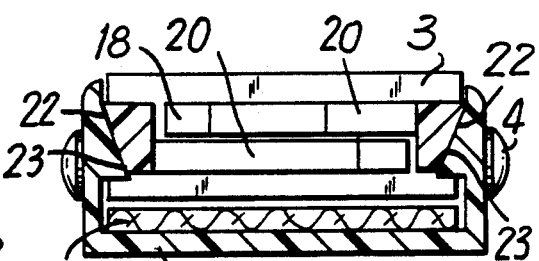
Figure 6:
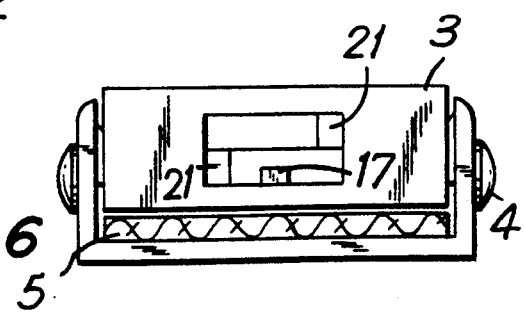
FIG. 6 is a view as seen in direction of the arrow VI in FIG. 4, in the opening position.

As shown in FIG. 4 a recess which is formed in the clamping rocker 3 for guiding the sliders 20 has inclines 24 which improve the engagement of the arresting cams 18 with the hooks 14 with increasing constricting pulling force in the band 5. Therefore it is guaranteed that with higher constricting force, undesirable release of the arresting closure 8 cannot occur.

FIGS. 7-10 show another embodiment in which the clamping rocker is not actuated, and after reaching its releasing position for releasing the band 5 a further turning is performed to obtain the opening position in which the arresting closure is additionally opened. Here, the sliding keys extend laterally from the closure housing 2 with actuating buttons 25. They cooperate with inclined running surfaces 27 of a wedge shaped projection 28 which is mounted on the clamping rocker 3 substantially in the region of the arrow 12 in FIG. 1. The actuating buttons 25 cooperate with vertical surfaces 29 on lateral end surfaces 30 of the sliders 20 which were described with reference to the embodiments of FIGS. 3-7.

Figure 7:
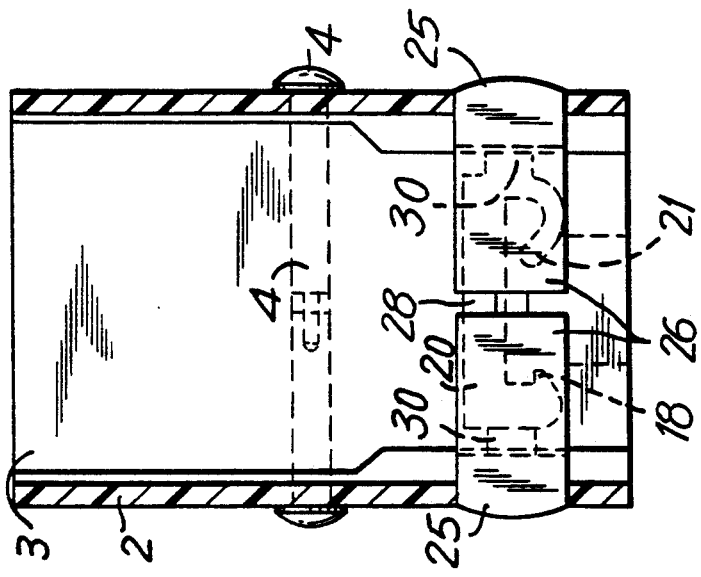
FIG. 7 is a plan view of an alternative embodiment of the closure housing.
Figure 9:
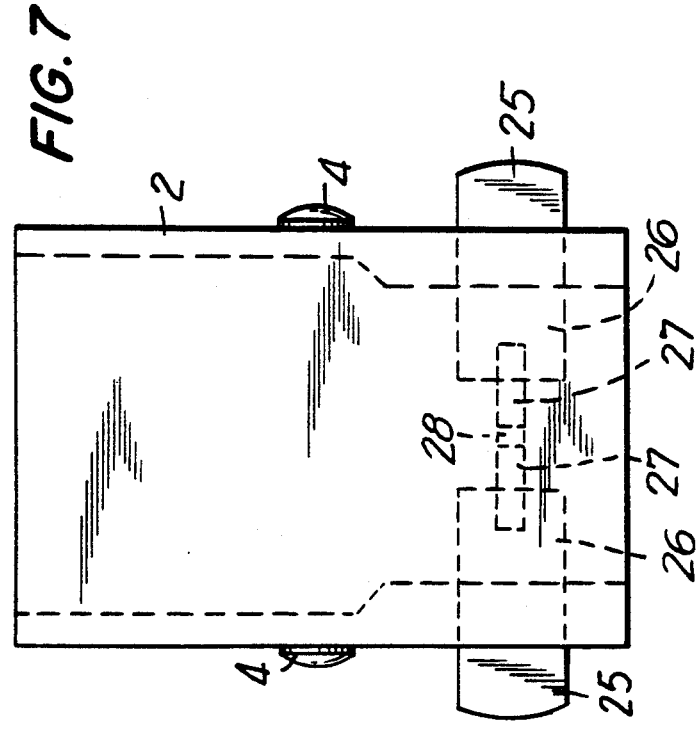
FIG. 9 is a view substantially corresponding to the view of FIG. 7, however, in form of a horizontal longitudinal section through the closure housing and in the opening position.
Figure 8:
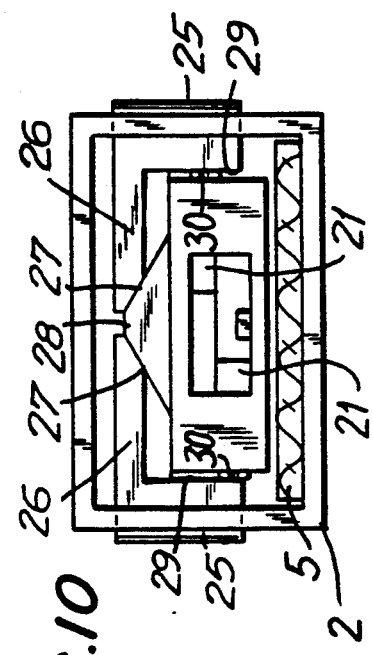
FIG. 8 is a view as seen in the direction of the arrow VIII in FIG. 7.
Figure 10:
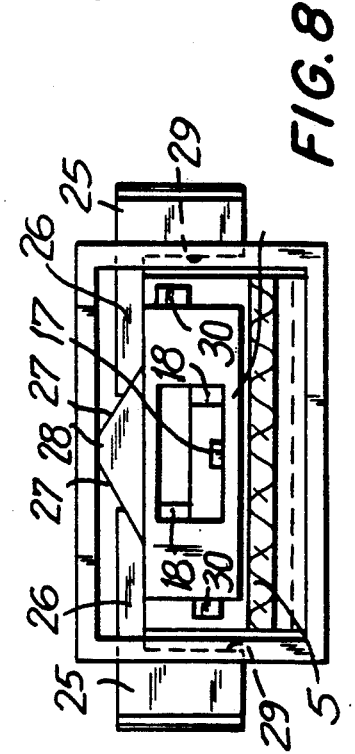
FIG. 10 is a view as seen in direction of the arrow X in FIG. 9.

FIGS. 7 and 8 in which the arresting components 8a and 8b are omitted, show the arrangement in the constricting position. In this position the clamping rocker is located in its clamping position and the sliding keys 26 can be laterally withdrawn by means of the wedge shaped projections 28. When the actuating buttons 25 are pressed opposite to one another, then due to the distance between the surfaces 29 and 30, first only the clamping key 3 is turned by the wedge shaped projection 28 and the inclined surface 27 to its releasing position. Then the surfaces 29, 30 come to abutment, and further the sliding pressure against the actuating button 25 leads to opening of the arresting closure. This condition is shown in FIGS. 9 and 10.

Figures 11, 12:
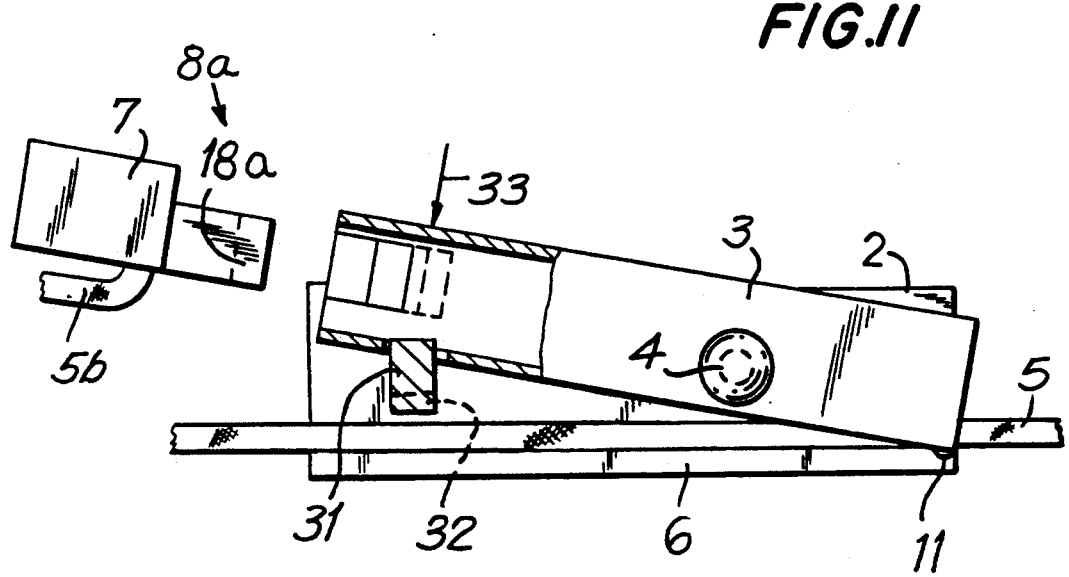
FIG. 11 is a schematic showing in a side view or central vertical longitudinal section of still another embodiment of the closure housing and the arresting closure.
FIG. 12 is a partially open plan view of the closure housing and the arresting closure of FIG. 11.

Another arrangement is illustrated in FIGS. 11 and 12. Here a block 31 is mounted centrally on a bridge 32 which is arranged above the band 5 between the side walls of the closure housing 2. The block 31 has side walls 23a which are twice inclined. The side walls diverge from above downwardly as can be seen in FIG. 12 and also from a front rearwardly. When in the arresting condition the inwardly extending hooks 18a of the arresting component 8a engage over the arresting cams 14a in the clamping rocker 3, corresponding inclined outer surfaces of the hooks 14a abut against the side walls 23a. Therefore when the clamping rocker 3 is turned by a pressing in direction of the arrow 33 in releasing and opening direction around the axle 4, after the releasing of the tension in the band 5 the hooks 18a are pressed outwardly in a springy fashion until they disengage from the arresting cams 14a and are displaced to the opening position shown in FIGS. 11 and 12.

In the above mentioned embodiments the opening actuation is not distinguished from the preceding releasing actuation by the operator or in the best case is distinguished by a different resistance (pressure point) of the participating actuating element. As a result during not sufficiently careful actuation the opening can lead to too fast release. In contrast, in the embodiment shown in FIGS. 13-16, a lock limits the actuation by reaching the releasing position and extends loosening of the actuation pressure for a short time so that the further actuation to the opening position can be performed by applying the actuating pressure again.

The clamping rocker 3 is supported via its elongated openings 40 on the axle 4 fixedly mounted in the housing 2 in a non-rotatable fashion, and is movable in a longitudinal direction to a limited extent in direction of the longitudinal axis 19 in FIG. 4. A spring 41 which is supported on the axle 4 acts on a curved leg 42 of the clamping rocker 3 and presses it to an opening position in which the elongated openings 4 abut with their left ends against the axle 4 as shown in FIG. 15.

Figure 13:
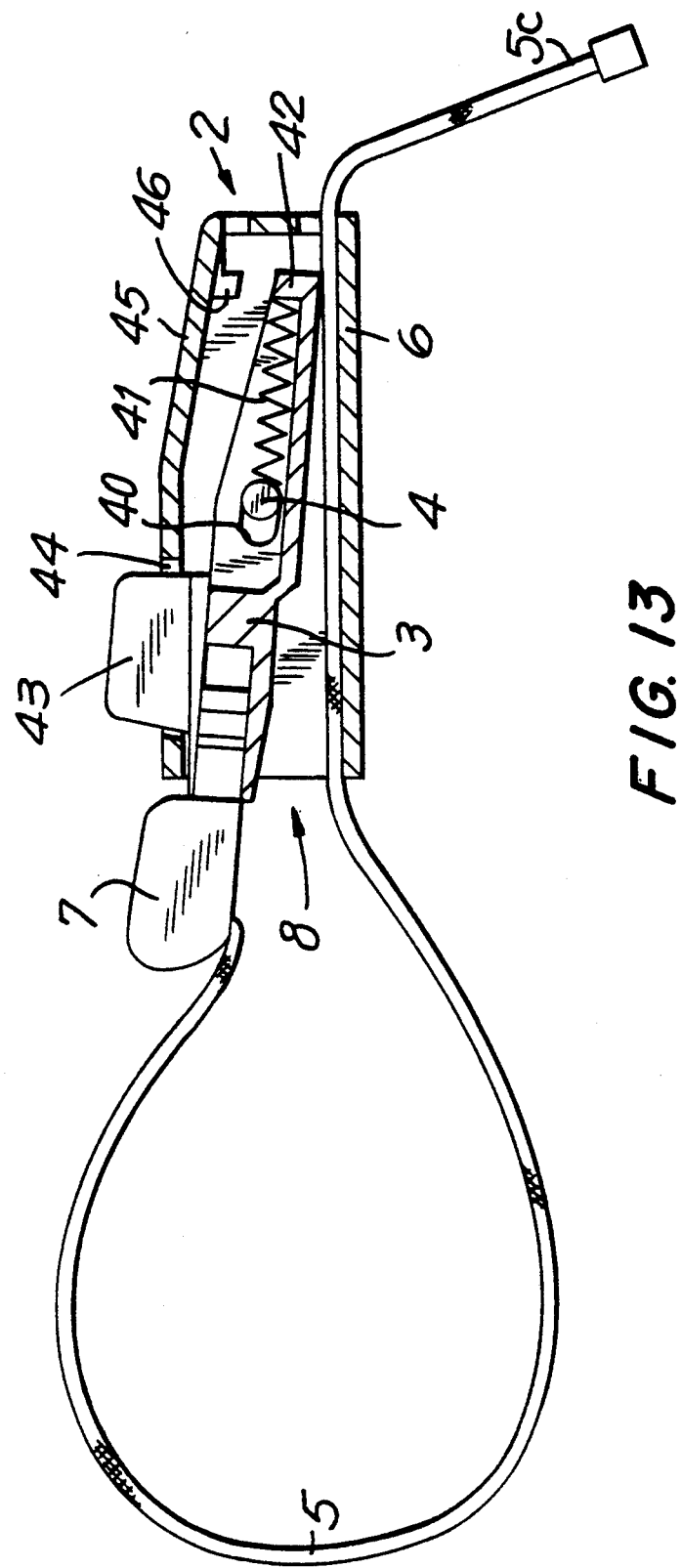
FIG. 13 is a view showing a restricting device with a different type of the closure housing and the arresting closure, in a central vertical longitudinal section and in the constricting position.

During applying of the constricting device, after closing of the arresting closure 8, the clamping rocker 3 due to the constricting pulling force in the band 5 is pulled against the force of the spring 41 to its position shown in FIG. 13, in which the right ends of the elongated openings 40 abut against the axle 4. When for releasing the constriction a pressure is applied to the push buttons 43 extending through an opening 44 of the closure housing 2 which is closed by a cover 45, the clamping rocker 3 is turned from its constricting position shown in FIG. 13 to its releasing position shown in FIG. 14. The bent leg 42 abuts against a stop 46 of the cover 45. When the pressure on the push button 43 is temporarily interrupted, the spring 41 can further turn the clamping rocker 3 to the opening position shown in FIG. 15, since now the projection 42 can pass the stop 46. Therefore the arresting closure 8 is opened.

Figure 16:
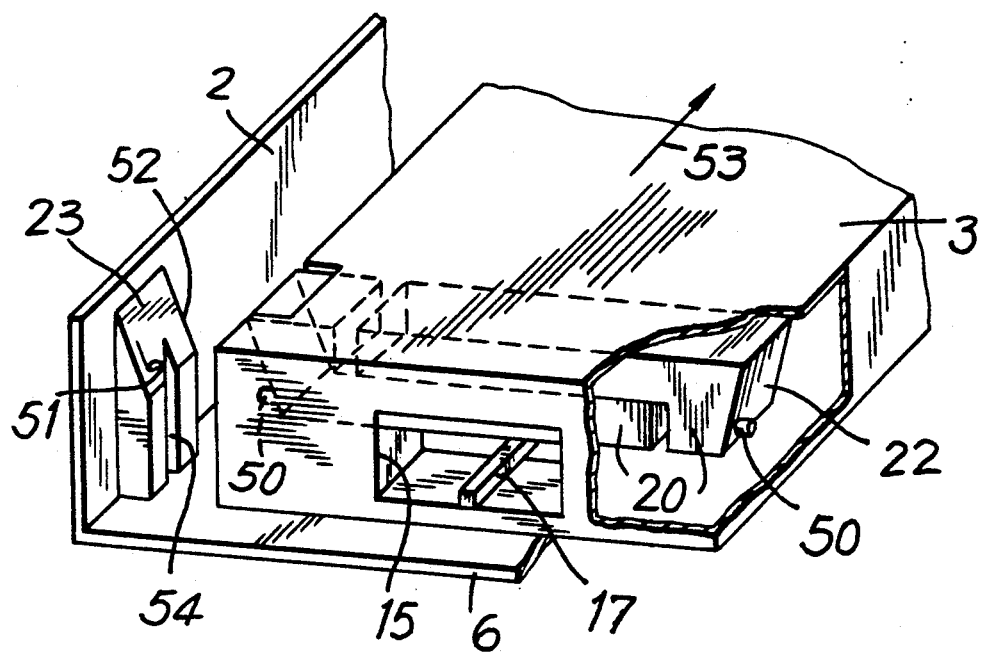
FIG. 16 is a partially sectioned exploded partial view of a different embodiment of a locking mechanism for catching the clamping rocker in the releasing position.

FIG. 16 shows a different embodiment of the lock which is used for preventing a stepless transition from the releasing position to the opening position and formed as a "catch nest". Here the wedge surfaces 22, 23 which are described in connection with FIGS. 3 and 4, are additionally provided with locking members which are offset relative to one another in a longitudinal direction. Pins 50 which are arranged on the sliders 20 are engaged at the end of the releasing actuation of the clamping rocker 3 into pocket-shaped depressions 51 in the opening sliders 52 provided with wedge surfaces 23. If the pressure on the clamping rocker in releasing or opening direction is loosened for a short time, it is pulled by a spring which corresponds to the spring 41 in direction of the arrow 53. Therefore during a new actuation the pin 50 engages in grooves 54 and the clamping rocker can be turned further in the opening direction. Thereby the cooperation of the wedge surfaces 22 and 23 leads to opening of the arresting closure.

Figure 14:
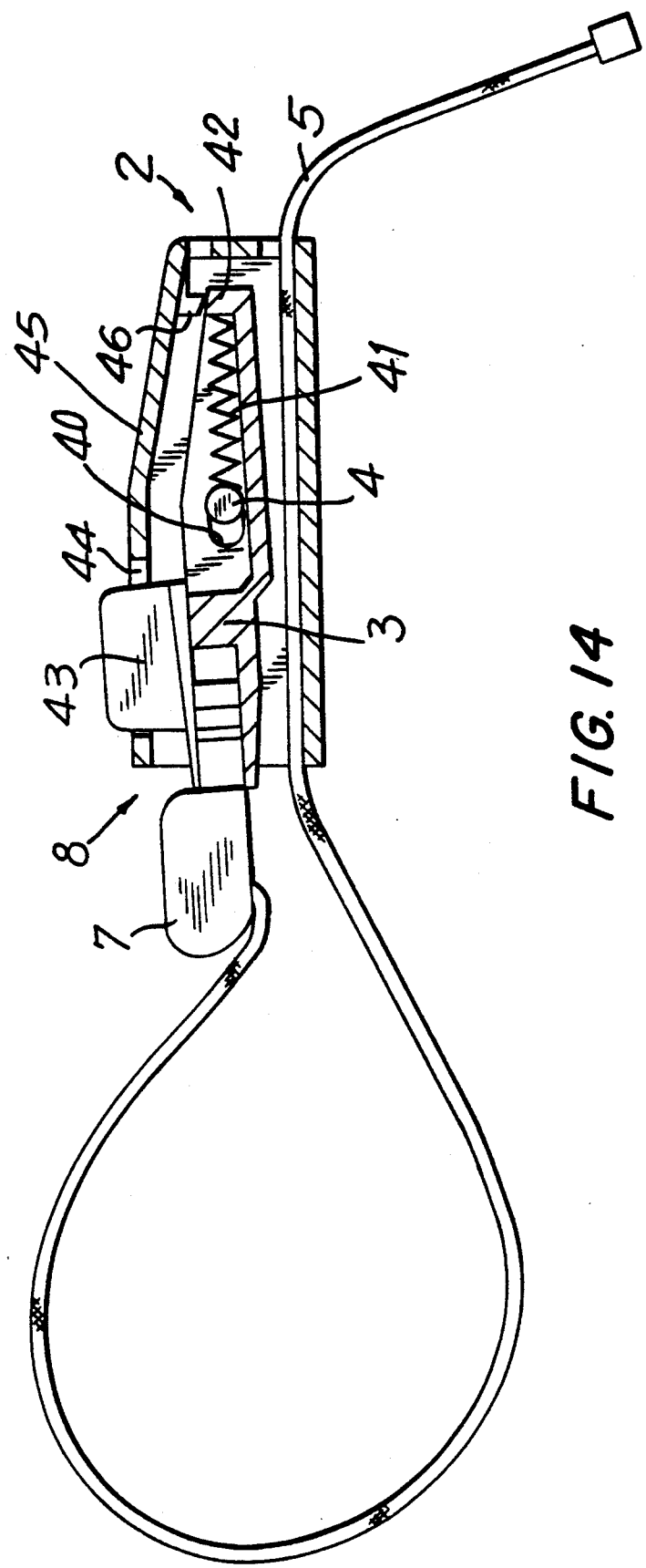
FIG. 14 is a view substantially corresponding to the view of FIG. 13 but in the releasing position.
Figure 15:
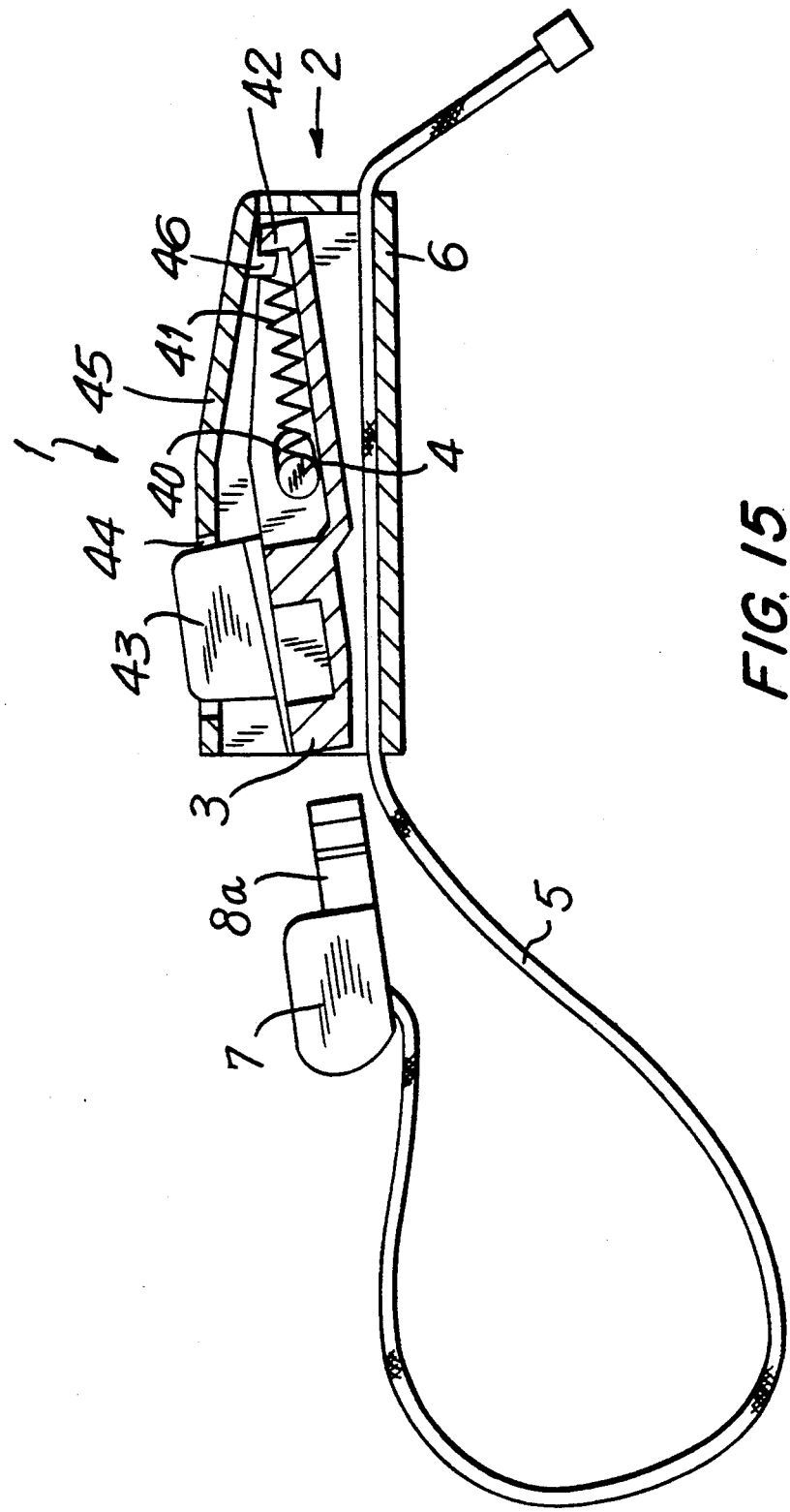
FIG. 15 is a view substantially corresponding to the views of FIGS. 13 and 14, but in the opening position.
Figure 17A:
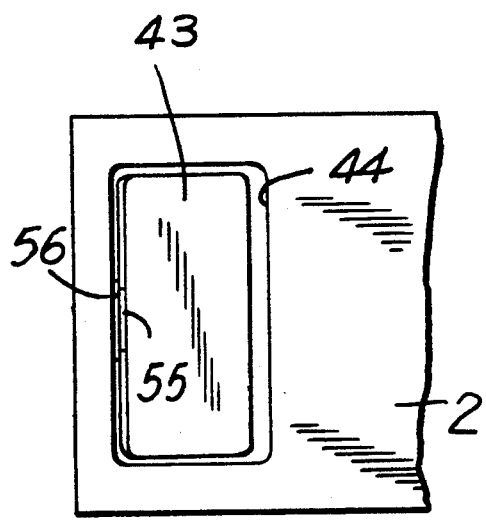
FIGS. 17a and 17b are sectional partial views of a push button which actuates the clamping rocker, with a device for producing a clicking sound during movement of the clamping rocker to the releasing position, in a plan view and in a schematic side sectional view.
Figure 17B:
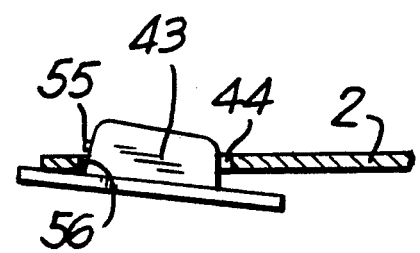

FIG. 17 schematically shows the arrangement of projections 55, 56 on the push buttons 43 for the embodiment of FIGS. 13-15 and the opening 44 provided in the cover of the closure housing 2 and surrounding the push button. During the releasing process the projection 55 passes the projection 56 and therefore a clicking sound is produced to signal to the operator that the releasing position is reached.

It will be understood that each of the elements described above, or two or more together, may also find a useful application in other types of constructions differing from the types described above.

While the invention has been illustrated and described as embodied in a constricting device for body parts, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for various applications without omitting features that, from the standpoint of prior art, fairly constitute essential characteristics of the generic or specific aspects of this invention.

What is claimed as new and desired to be protected by Letters Patent is set forth in the appended claims:

1. A constricting device for body parts, comprising a housing; a clamping rocker rotatably supported in said housing, said clamping member being rotatable between a clamping position in which one end of said clamping rocker clamps a band extending through said housing against a housing wall and an opposite releasing position in which it releases said band, said clamping rocker, when said band which is in a constricting position under tension, being rotated in one direction to said clamping position under the action of the tension while a manual actuating pressure applied to said clamping rocker rotates said clamping rocker in an opposite direction to said releasing position; a releasable arresting closure provided between another end of said clamping rocker and an end of the band; and a mechanical transmission member cooperating with said clamping rocker and with said arresting closure so that during applying the manual actuating pressure to said clamping rocker said mechanical transmission member first, rotates said clamping rocker to said releasing position and then after a release of said band opens said arresting closure.

2. A constricting device as defined in claim 1; and further comprising a cap arranged on said end of the band, said arresting closure operating between said another end of said clamping rocker and said cap.

3. A constricting device as defined in claim 1, wherein said transmission member is formed so that during rotating of said clamping rocker from said clamping position said transmission member first provides in said releasing position of said clamping rocker an operative connection to said arresting closure and then opens said arresting closure during a further rotating of said clamping rocker.

4. A constricting device as defined in claim 1, wherein said transmission member is formed so that said transmission member during application of the actuating pressure for opening of said arresting closure counteracts a greater resistance than a resistance which is to be overcome for releasing of the band by said clamping rocker.

5. A constricting device as defined in claim 4; and further comprising a spring producing a closing force which pressures said arresting closure to a closing position and counteracts an opening actuation of said arresting closure with a greater force component than the tension applied by the band in its constricting position to said clamping rocker applies in the clamping position.

6. A constricting device as defined in claim 1; and further comprising a lock which blocks an action of said transmission member until an interruption of the manual actuating pressure after the release of the band.

7. A constricting device as defined in claim 1; and further comprising a turning axle provided for said clamping rocker and longitudinally displaceable in said housing; a spring arranged so that the band in its constricting position pulls said clamping rocker against a force of said spring to a first end position; a stop arranged so that in said first end position during manual pressure actuation of said clamping rocker a rotating movement of said clamping rocker is limited by said stop so that said clamping rocker can only reach the releasing position, and then after releasing of the band said spring moves said clamping rocker beyond the stop to a second end position in which said clamping rocker can be rotated further to open said arresting closure.

8. A constricting device as defined in claim 7, wherein said stop has a portion which extends substantially perpendicularly to said clamping rocker and prevents a longitudinal displacement of said clamping rocker under a spring force until said clamping rocker is rotated back to the releasing position.

* * * * *